United States Patent [19]

Denton et al.

[11] Patent Number: 4,688,942
[45] Date of Patent: Aug. 25, 1987

[54] RADIAL AND AZMUTHAL NON-RESONANT OPEN-TUBULAR OPTOACOUSTIC CELL

[75] Inventors: Medona B. Denton, Tuscon, Ariz.; Scott B. Tilden, Brunswick, Ohio

[73] Assignee: The United State of America as represented by the Secretary of the Navy, Washington, D.C.

[21] Appl. No.: 777,474

[22] Filed: Sep. 18, 1985

Related U.S. Application Data

[63] Continuation-in-part of Ser. No. 445,321, Nov. 26, 1982.

[51] Int. Cl.$^4$ .................. G01N 21/01; G01N 21/59
[52] U.S. Cl. ..................................... 356/432; 356/440
[58] Field of Search ........................... 356/432 T, 440

[56] References Cited

U.S. PATENT DOCUMENTS 4,277,179  7/1981  Bruce .................................. 356/433
4,325,252  4/1982  Miller et al. ..................... 356/432 T

OTHER PUBLICATIONS

Kreuzer, L. B., "Ultralow Gas Concentration Infrared Absorption Spectroscopy", *Journal of Applied Physics*, vol. 42, No. 7 (Jun. 1971), pp. 2934–2943.

Patel et al, "A New Optoacoustic Cell with Improved Performance", *Appl. Phys. Lett.*, vol. 30, No. 11 (1 Jun. 1977), pp. 578–579.

Gerlach et al, "Brewster Window and Windowless Resonant Spectrophones for Intracavity Operation", *Appl. Phys.*, vol. 23, No. 3 (Nov. 1980), pp. 319–326.

White, Harvey, *"Modern College Physics"*, fourth edition, copyright 1962, D. Van Nostrand Company, Inc., New York, pp. 275–277.

*Primary Examiner*—R. A. Rosenberger
*Attorney, Agent, or Firm*—Thomas M. Phillips

[57] ABSTRACT

A radial or azmuthal non-resonant flow-through optoacoustic cell is operated without windows, completely eliminating the window background interference. The cell is constructed of an elongated tube the length of which is $34 \times 10^3 \text{cm} \times 1/f$, where f is the light source modulating frequency and is made of conducting material which is perforated along the center one-half length with holes. A metalized sheath surrounds this center region to form a capacitor microphone.

4 Claims, 2 Drawing Figures

RADIAL AND AZMUTHAL NON-RESONANT OPEN-TUBULAR OPTOACOUSTIC CELL

This invention is a continuation-in-part of U.S. patent application Ser. No. 445,321, filed Nov. 26, 1982.

BACKGROUND OF THE INVENTION

The present invention relates to optoacoustic spectroscopy and more particularly to optoacoustic spectroscopy for detecting trace gases at the part-per-billion level.

There is interest in optoacoustic spectroscopy of detecting trace gases at the part-per-billion level. However, there is a problem of large window background signals in using conventional optoacoustic cells. Many attempts have been made to eliminate this background signal. These attempts include the differential cell, multipass cell, and windowless resonant cell.

The window background signal in optoacoustic spectroscopy arises whenever a modulated light source passes through any window material. In conventional optoacoustic cells, window background is generated from the two windows at each end of the cell. This signal is thought to be generated at the window-gas interfacial region, with the magnitude of this signal dependent on the heat capacity of the window material. Given the choice of the window materials used in the IR region (sapphire, germanium, ZnSe, NaCl, KCl, etc.), all have similar heat capacities making the window background problem ubiquitous.

The obvious solution to the window background problem would be to eliminate the windows in a non-resonant cell altogether. However, in conventional non-resonant cells this is not possible due to the need to confine the pressure wave in the cell such that this energy can be used to move the diaphragm of the microphone. Except for an infinitely sensitive microphone, more energy is expended moving the diaphragm than is used to vent the pressure wave out of the cell. Such a cell is described by Kreuzer, L. B., J. Appl. Phys., 42 (7), June 1971, p. 2934–2943.

The pressure-time response of the short (5 cm) cell described by Kreuzer operating in the windowless mode is such that only a very weak signal will be detected requiring very sensitive equipment. Immediately after the source beam is "turned on" to full intensity, analyte gas may absorb energy from the source light beam. Absorbed energy will be almost instantaneously transferred to translational energy, causing a temperature and pressure rise in the cell. The pressure rise in the cell will be sensed by the microphone diaphragm producing a momentary signal as the microphone diaphragm expands against ambient gas pressure. In response to the thermally perturbed environment in the cell, gas will flow out of the cell as a pressure wave at the speed of sound. The amplitude of the pressure wave will be such that thermal equilibrium will be established between gas in the cell and the environment according to the universal gas law. For the 5 cm long cell, approximately 0.074 millisecond is needed for the pressure wave originating at the center of the cell to exit either end of the cell. Assuming a 50% duty cycle modulation of the light source beam, the beam will transverse the cell during the "on-state" for 1.25 millisecond. Therefore, the pressure pulse will be detected for approximately 6% of the total "on-time" of the light source. Likewise, when the laser is "turned off" another pressure wave is generated by gases re-entering the cell. Because the pressure wave exists for only 6% of the total time the light source is on (or off), a relatively small signal will be observed from the microphone when operating a "short" cell in the windowless mode.

SUMMARY OF THE INVENTION

The present invention provides for a open-tubular non-resonant cell that dynamically contains the bulk of the pressure wave in the cell without the use of windows. A cell is provided wherein the path length is sufficiently long in relation to the chopping frequency of the laser beam to dynamically contain the pressure pulses. The length of the cell should ideally be $34 \times 10^3 c \times 1/f$ is the light source modulation frequency.

The open-tubular non-resonant cell is constructed of an elongated tube made of conducting material which is perforated along the center one-half length with rows of holes. A metalized sheath is wrapped around this center region keeping the distance between the tube and the sheath separated by plastic spacers and being sealed at each end of the sheath. By providing a biasing voltage connection to the metallic sheath, the tube and sheath form the two plates of a capacitor microphone.

OBJECTS OF THE INVENTION

Accordingly, an object of the invention is the provision of an extended length, non-resonant optoacoustic cell employing dynamic pressure confinement.

Another object of the invention is the provison of a open-tubular cell for optoacoustic spectroscopy which has the ability to operate in a flow through mode.

Another object of the invention is the provision of a open-tubular cell for optoacoustic spectroscopy which has reduced effects from the previous sample.

A further object of the invention is the provision of a open-tubular cell for optoacoustic spectroscopy which may be made to operate effectively over a wide range of chopping frequencies.

Still another object of the invention is the provision of an extended length, non-resonant optoacoustic cell employing dynamic pressure confinement, the length being substantially $34 \times 10^3 \times 1/fcm$, where f is the light source modulating frequency.

Other objects, advantages and novel features of the invention will become apparent from the following detailed description of the invention when considered in conjunction with the accompanying drawings wherein.

Figures 1, 2:
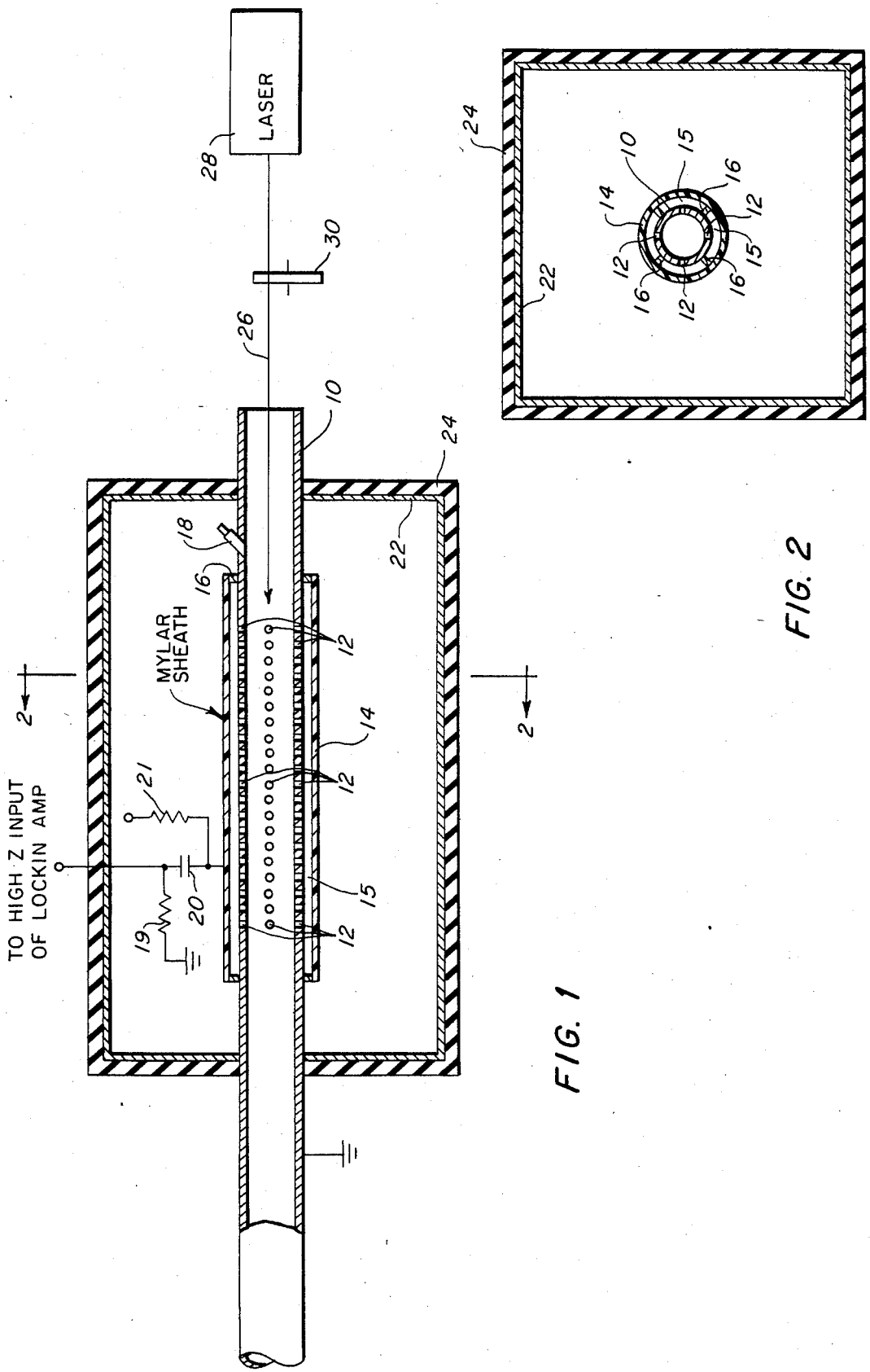
FIG. 1 is a schematic diagram of the windowless non-resonant cell showing the cell in cross-section.
FIG. 2 is a cross-section of the cell of FIG. 1 taken along the lines 2—2.

Referring now to the drawings wherein there is shown in FIGS. 1 and 2 the preferred embodiment of the invention. The windowless non-resonant cell is constructed of an elongated tube 10 perforated along the center one-half length with four rows of holes 12 spaced apart. Each row of holes is 90 degrees from the row adjacent to it. An aluminized Mylar sheath 14 is wrapped around the center region. The distance between tube 10 and the sheath 14 is kept separated to form an air space 15 by plastic spacers 16 at each end of the sheath 14. For purposes of flushing the cell a fitting 18 to which a source of gas may be connected is mounted in tube 10. A biasing network consisting of resistors 19 and 21 and capacitor 20 is connected to Mylar sheath 14.

A rectangular metal chassis 22 is placed around the cell to protect the high resistance biased capacitor microphone from electrical noise. Chassis 22 is covered with foam rubber 24 to damp out any acoustical interference that might be present.

In operation and by way of example, a laser beam 26 originating from laser 28 and being chopped by chopper 30 at a chopping rate of 400 Hz is beamed through tube 10. Tube 10 is constructed of a 90 cm×1.27 cm OD extruded aluminum tube with a wall thickness of 0.159 cm. Tube 10 is perforated along the center one-half length with four rows of 30 holes (0.3 cm dia.) spaced 90 degrees from the adjacent row. An aluminized Mylar sheath 14 (Mylar - A 3 mils thick) 50 cm long is wrapped around the center region. The distance between sheath 14 and tube 10 is 0.15 cm.

A modulation frequency of 400 Hz is assumed for the light source modulation frequency. Typically, an optimum frequency will be found that will minimize background room noise effects (the intensity of this noise is usually proportional to inverse frequency) and still provides a reasonably intense optoacoustic signal. A pressure wave (at STP) can transverse 85 cm during one light source modulation cycle. Ideally, the cell length should approximate this dimension.

The 90 cm open-tubular cell cell can operate in the windowless mode because approximately 1.3 millisecond is necessary for a pressure wave originating in the center of the cell to exit either end of the cell. This time is approximately equal to the "on-time" of the light source modulated at 400 Hz (50% duty cycle), thus the pressure wave can be sensed for the total on (or off) time of the light source. Therefore, the signal intensity of the "long" cell operated in the windowless mode will approach the signal that would be observed in a cell that contained windows.

Obviously many modifications and variations of the present invention are possible in the light of the above teachings. It is therefore to be understood that within the scope of the appended claims the invention may be practiced otherwise than as specifically described.

What is claimed is:

1. An optoacoustic spectroscopy system with an open tubular azmuthal and radially non-resonant flow through cell including:
    a laser source for directing a laser beam through said cell,
    chopping means positioned in the path of said laser beam for chopping said laser beam at a predetermined frequency,
    said cell comprising
    a duct through which a sample of gas to be analyzed can flow and through which said laser beam chopped at said predetermined frequency is beamed,
    said duct having a portion thereof surrounded by a chamber,
    said duct having openings between said duct and said chamber whereby changes in pressure within said duct will be transmitted to said chamber,
    the length of said duct being of sufficient length in relation to said chopping frequency of the laser beam so that pressure pulses generated by laser excitation within the cell will remain in said duct for the total off time of said chopped laser beam.

2. The cell of claim 1 wherein said chamber is formed between conducting means surrounding a portion of said duct and the outer surface of said duct, said conducting means being insulated from said duct to form one plate of a capacitor microphone, with said openings being between said duct and said conducting means whereby changes in pressure within said duct will be sensed by said microphone.

3. The open tubular cell of claim 1 wherein said duct length is approximately $1/(f * 34 * 10^3)$cm, where f is said predetermined frequency.

4. The open-tubular cell of claim 3 wherein said duct length is approximately 90 cm and said predetermined frequency is approximately 400 Hz.

* * * * *